(12) United States Patent
Corstjens et al.

(10) Patent No.: US 7,858,396 B2
(45) Date of Patent: Dec. 28, 2010

(54) LATERAL FLOW ASSAY DEVICE WITH MULTIPLE EQUIDISTANT CAPTURE ZONES

(75) Inventors: Paul L.A.M. Corstjens, Leiderdorp (NL); Keith Kardos, Bethlehem, PA (US); R. Sam Niedbala, Allentown, PA (US); Hans J. Tanke, Leiden (NL); Michel Zuiderwijk, Alphen (NL); Hans H. Feindt, Catonsville, MD (US); Vijay K. Mokkapati, Macungie, PA (US); Jess Aaron Kimball, Portland, OR (US)

(73) Assignee: Orasure Technologies, Inc., Bethlehem, PA (US)

( * ) Notice: Subject to any disclaimer, the term of this patent is extended or adjusted under 35 U.S.C. 154(b) by 301 days.

(21) Appl. No.: 11/589,943

(22) Filed: Oct. 31, 2006

(65) Prior Publication Data

US 2007/0105237 A1 May 10, 2007

Related U.S. Application Data

(60) Provisional application No. 60/731,485, filed on Oct. 31, 2005.

(51) Int. Cl.
*G01N 33/53* (2006.01)

(52) U.S. Cl. ............ 436/514; 436/518; 436/169; 436/172; 436/175; 436/530; 436/533; 436/807; 436/170; 436/823; 422/56; 422/57; 422/58; 422/59; 422/60; 435/287.7; 435/287.9; 435/7.1; 435/7.92; 435/7.93; 435/823; 435/805

(58) Field of Classification Search ............ 435/823, 435/287.7, 287.9, 805, 7.1, 7.91, 7.92, 7.93; 436/514, 518, 169, 172, 175, 530, 533, 807, 436/170, 823; 422/56, 57, 58, 59, 60
See application file for complete search history.

(56) References Cited

U.S. PATENT DOCUMENTS 4,703,017 A 10/1987 Campbell et al.

(Continued)

FOREIGN PATENT DOCUMENTS

WO  WO 88/08534  * 11/1988

OTHER PUBLICATIONS

Niedbala, R.S., et al., "Detection of Analytes by Immunoassay Using Up-Converting Phosphor Technology", Analytical Biochemistry, vol. 293, 2001, pp. 22-30.

(Continued)

*Primary Examiner*—Bao-Thuy L Nguyen
(74) *Attorney, Agent, or Firm*—J.A. Lindeman & Co., PLLC

(57) ABSTRACT

A lateral flow test strip for the analysis of a sample featuring numerous capture zones arranged in an array such that each capture zone is substantially equidistant from the sample containing area. The sample does not pass through another capture zone to reach any one of the other capture zones. The capture zones are preferably arranged in a linear array perpendicular to the flow of the sample through the lateral flow test strip. The lateral flow test strip allows for an increased number of simultaneous analyses of numerous analytes from one sample to occur on one lateral flow test strip.

23 Claims, 7 Drawing Sheets
(6 of 7 Drawing Sheet(s) Filed in Color)

U.S. PATENT DOCUMENTS

| | | | |
|---|---|---|---|
| 5,043,265 | A | 8/1991 | Tanke et al. |
| 5,591,645 | A | 1/1997 | Rosenstein |
| 5,654,162 | A | 8/1997 | Guire et al. |
| 5,728,587 | A * | 3/1998 | Kang et al. ............... 436/518 |
| 5,891,656 | A | 4/1999 | Zarling et al. |
| 6,103,536 | A * | 8/2000 | Geisberg ................ 436/518 |
| 6,203,757 | B1 * | 3/2001 | Lu et al. .................. 422/58 |
| 6,267,722 | B1 | 7/2001 | Anderson et al. |
| 6,855,561 | B2 * | 2/2005 | Jerome et al. ............ 436/514 |

OTHER PUBLICATIONS

Corstjens, P.L.A.M., et al., "Infrared Up-Converting Phosphors for Bioassays", IEE Proceedings—Nanobiotechnology, vol. 152, No. 2, Apr. 2005, pp. 64-72.

Deelder, A.M., et al., "*Schistosoma*: Analysis of Monoclonal Antibodies Reactive with the Circulating Antigens CAA and CCA", Parasitology, vol. 112, Part 1, Jan. 1996, pp. 21-35.

Coico, R., et al., "Immunology: A Short Course", Fifth Edition, John Wiley & Sons, Inc., Publication (Table of Contents), 2003.

Zuiderwijk, M., et al., "An Amplification-Free Hybridization-Based DNA Assay to Detect *Streptococcus pneumoniae* Utilizing the Up-Converting Phosphor Technology", Clinical Biochemistry, vol. 36, No. 5, Jul. 2003, pp. 401-403.

Corstjens, P.L.A.M., et al., "Lateral-Flow and Up-Converting Phosphor Reporters to Detect Single-Stranded Nucleic Acids in a Sandwich-Hybridization Assay", Analytical Biochemistry, vol. 312, No. 2, Jan. 2003, pp. 191-200.

Corstjens, P.L.A.M., et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection", Clinical Chemistry, vol. 47, No. 10, 2001, pp. 1885-1893.

Carter, L., "Introduction", Advanced Dental Research, vol. 18, Jun. 2005, p. 1.

Li, Y., et al., "The Oral Fluid MEMS/NEMS Chip (OFNMC): Diagnostic & Translational Applications", Advanced Dental Research, vol. 18, Jun. 2005, pp. 3-5.

Smoot, L.M., et al., "DNA Microarrays as Salivary Diagnostic Tools for Characterizing the Oral Cavity's Microbial Community", Advanced Dental Research, vol. 18, Jun. 2005, pp. 6-11.

Malamud, D., et al., "Point Detection of Pathogens in Oral Samples", Advanced Dental Research, vol. 18, Jun. 2005, pp. 12-16.

Streckfus, C., et al., "The Use of Soluble, Salivary c-*erb* B-2 for the Detection and Post-Operative Follow-Up of Breast Cancer in Women: The Results of a Five-Year Translational Research Study", Advanced Dental Research, vol. 18, Jun. 2005, pp. 17-24.

* cited by examiner

Example 1 - Results
*Dilution series of DIG-biotin DNA*

Panel A: Inventive LF strip
Panel B: Conventional UPT-LF strip

Example 2 - Results
An example demonstrating the principle of target labeling

Example 3 - Results
Schistosomas CAA-sandwich assay

LATERAL FLOW ASSAY DEVICE WITH MULTIPLE EQUIDISTANT CAPTURE ZONES

CROSS-REFERENCE TO RELATED APPLICATION

This application claims priority to U.S. patent application Ser. No. 60/731,485, filed Oct. 31, 2005, which is incorporated herein by reference in its entirety.

GOVERNMENT FUNDING

This invention was made with government support under grant UO1-DE-014964 awarded by the National Institutes of Health. The government has certain rights in the invention.

BACKGROUND OF THE INVENTION

1. Field of the Invention

The invention relates generally to an assay device with multiple capture zones located substantially equidistant from a sample receiving area, and arranged in a linear array perpendicular to the sample path out of the sample receiving area. More particularly, the sample contacts each one of the multiple capture zones without passing through another capture zone thereby allowing for efficient testing for multiple target analytes in a single sample.

2. Description of the Related Art

Various lateral flow assay methods are utilized to test for the presence or, absence, or quantity of an analyte in a biological sample. A "sandwich" assay method, for example, uses an antibody immobilized on a solid support, which forms part of a sandwich with a labeled antibody, to determine the presence of a target analyte by observing the presence and amount of bound analyte-labeled antibody complex. In a competition assay, antibody is bound to a solid surface and then contacted with a sample containing both an unknown quantity of antigen analyte and labeled antigen of the same type. An indirect measure of the concentration of antigen analyte in the sample is provided by the measured amount of labeled antigen bound to the solid support. Numerous assay methods such as these may be performed on a lateral flow test strip.

Conventional lateral flow test strips feature a solid support on which the sample receiving area and the target capture zones are supported. The solid support material is one which is capable of supporting the sample receiving area and target capture zones and providing for the capillary flow of sample out from the sample receiving area to the target capture zones when the lateral flow test strip is exposed to an appropriate solvent or buffer which acts as a carrier liquid for the sample. General classes of materials which may be used as support include organic or inorganic polymers, and natural and synthetic polymers. More specific examples of suitable solid supports include, without limitation, glass fiber, cellulose, nylon, crosslinked dextran, various chromatographic papers and nitrocellulose. One particularly preferred material is nitrocellulose. See, for instance, U.S. Pat. Nos. 6,267,722, 5,654,162, 5,591,645 and 4,703,017.

Traditional lateral flow test strips contain one or more target capture lines. These capture lines are located on the strip parallel with the sample receiving area such that the flow of the sample from a sample receiving area sequentially contacts each of the capture lines. Sample aliquots are deposited onto a sample receiving area of the lateral flow test strip which may then be exposed to a solvent or carrier liquid which flows across the strip, and carries the sample material across the target capture zones toward an absorbent pad located at the end of the test strip. These features are illustrated in FIG. 1 with a lateral flow test strip with the various capture lines aligned parallel to the sample receiving area and the flow of the sample out of the sample receiving area contacting sequentially each capture line. The conventional lateral flow test strips are constructed for use with commercially available readers and thus are sized to fit in a specific sized plastic housing. The housing typically has an upper part with an opening for sample application to the sample pad and another opening or window over the capture lines to read the results of the assay.

There is a limit to the number of target capture lines that can be used with the conventional lateral flow assay format. The limit arises, in part, because succeeding capture lines, located further away from the sample pad, suffer from the non-specific capture of sample and analyte by the preceding capture zones and the materials used to construct the assay device. This non-specific capture, which also occurs in the assay strip material itself, results in the sample supply becoming exhausted prior to contacting all target capture lines. Locating target capture zones further away from the sample receiving area decreases signal intensity. This loss of signal intensity may then affect sensitivity. Clearly there is a need to minimize the occurrence and effects of non-specific analyte capture on a lateral flow test strip.

One lateral flow assay technique of particular interest is the UPT-LF (Upconverting Phosphor Technology-Lateral Flow) assay method which utilizes up-converting phosphor microparticles as labels on lateral flow test strips. The UPT-LF technology may be utilized in, for instance, sandwich or competitive formats for the analysis of, for instance, drugs, drug metabolites, or other substances, such as, antigens, proteins, and DNA. It has been shown (Corstjens et al., Clin. Chem., 2001, 47, pp. 1885-1893; Corstjens et al., Anal. Biochem., 2003, 312, pp. 191-200, 2003; Zuiderwijk et al. Clin. Biochem., 2003, 36, pp. 401-403) that besides the conventional antibody-antigen UPT-LF assays, nucleic acid UPT-LF assays have also been developed. Clearly, the possible detection of both proteins and nucleic acids from one sample on one lateral flow test strip is likely to further increase complexity of the assay, the sample and the lateral flow capture zones. Thus, there is a need for an assay strip which easily permits more numerous analyses in a single test.

SUMMARY OF THE INVENTION

The invention is a lateral flow test strip comprising a sample receiving area for receiving a sample for analysis, and two or more analyte capture zones. The analyte capture zones are substantially equidistant to the sample receiving area, and are arranged in a linear array perpendicular to a flow of the sample from the sample receiving area.

A method of analyzing for an analyte comprising the step of applying a sample to a lateral flow test strip is another embodiment of the invention. Here, the lateral flow test strip comprises a sample receiving area for receiving a sample for analysis and two or more analyte capture zones, and the analyte capture zones are arranged in a linear array perpendicular to a flow of the sample from the sample receiving area and substantially equidistant to the sample receiving area.

Yet another embodiment of the invention is a method of preparing lateral flow test strips comprising the step of applying analyte capture compositions to a lateral flow test strip to form analyte capture zones, wherein the analyte capture zones are arranged in a linear array perpendicular to a flow of the sample from a sample receiving area and substantially equidistant to the sample receiving area.

The invention addresses the problem of sample exhaustion by non-specific analyte capture occurring in existing assay devices and permits the simultaneous testing of numerous different analytes present in one sample. Specifically, two or more zones of analyte capturing compositions, or target capture molecules, are immobilized on the test strip substantially equidistant from the sample receiving area and in a linear array which is perpendicular to the sample flow rather than parallel to the flow of the sample. The placement of capture or test zones substantially equidistant from the sample receiving area and in a linear array perpendicular to the sample flow direction eliminates differences in sample concentration which can occur when the sample passes through other capture zones prior to contacting every other capture zone. The capture zones may be prepared using techniques and materials known for use in lateral flow assays. The capture reagent may vary on depending on the type of lateral flow assay and the analyte of interest, as is know in the art. Examples of analyte capture reagents, or target capture molecules, include, for instance, antibodies, antigens, proteins (natural, synthetic or fragments) and other nucleic acids. Any macro-molecule having an appropriate binding affinity in any biological interaction is applicable for purpose of target capture.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION

The invention is a transverse lateral flow test strip having a sample receiving area for receiving a sample for analysis, and two or more analyte capture zones, wherein the analyte capture zones are arranged in a linear array perpendicular to the flow of the sample out of the sample receiving area and substantially equidistant. Various aspects of the invention have been described in Malamud, et al., "Point Detection of Pathogens in Oral Samples", Adv. Dent. Res. 18:12-16, June, 2005 and Corstjens et al., "Infrared up-converting phosphors for bioassays", IEE Proc.-Nanobiotechnol., 152:64-72 (2005), both of which are incorporated here by reference. The transverse lateral flow test strips of the invention and their methods of use can employ existing lateral flow assay technology. The assays may be "visual read" assays using, for example, particulate label reagents to show the presence of an analyte or "instrument read" assays where the presence of the analyte is detected using an instrument to detect a signal. The reagents used in the assays on the transverse lateral low test strip may be the same as those used for known lateral flow assays. An advantage of the transverse lateral flow assays, as discussed herein, is the ability to place multiple assays on the test strip.

In the transverse lateral flow assays of the invention, the capture zones may be placed by hand, although for commercial production, the capture zones and any other reagent zones on the assay may be placed using production techniques known in the art of making lateral flow assay strips. There may be scatter when capture zones are prepared "by hand", though probably less than 0.5 mm. A template or mold may be designed and used to improve placement and reduce scatter. Any such scatter can be reduced or eliminated in machine produced tranverse lateral flow test strips, for example when using a Bio-Dot machine. The analyte capture zones may be disk or dot shaped pinpoint areas. As in known lateral flow assays the capture zones contain analyte capture reagents. The amount of the analyte capture reagent in a capture zone ranges from about 1 nanoliter to about 1 microliter.

Figure 1:
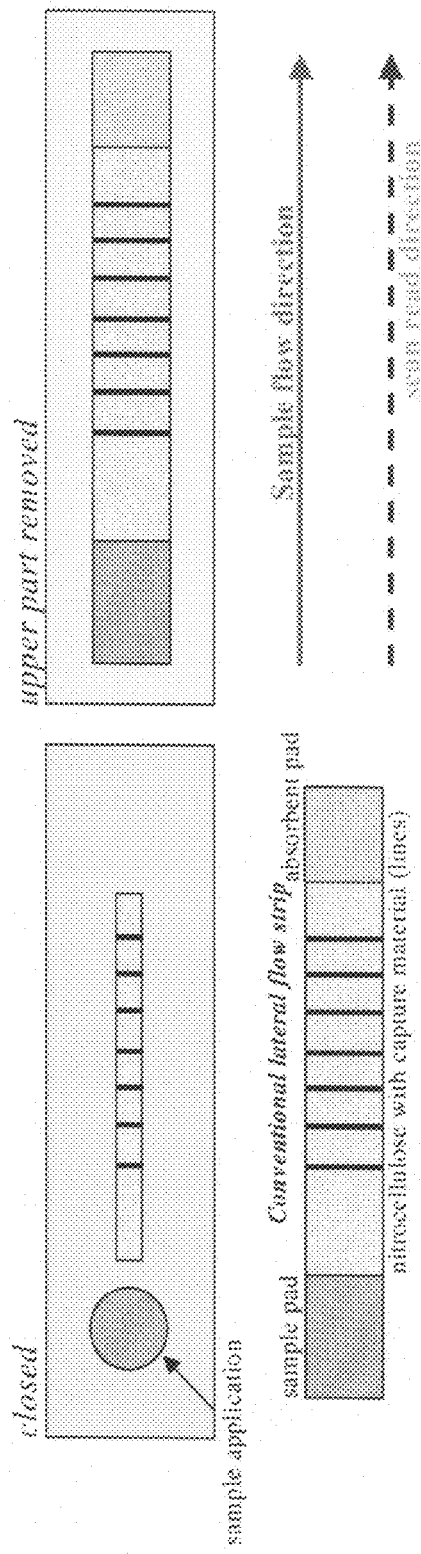
FIG. 1 illustrates a conventional lateral flow test strip mounted in a conventional housing.
Figure 2:
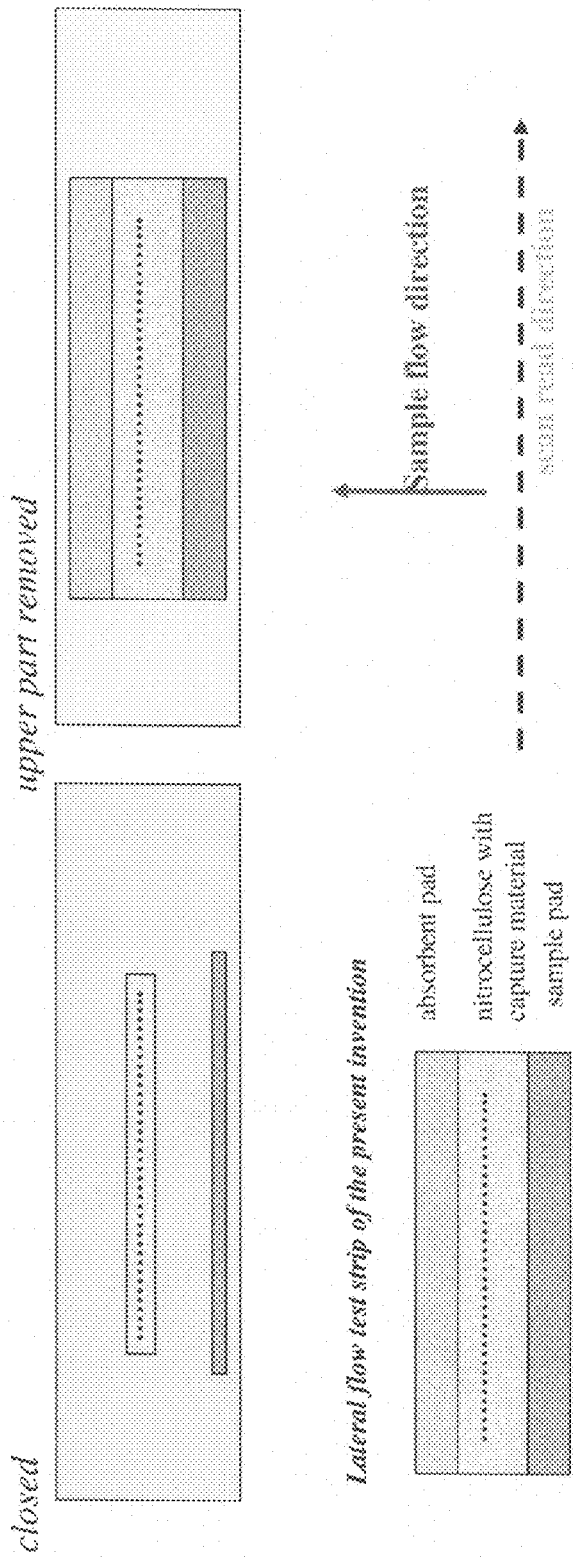
FIG. 2 illustrates one embodiment of the inventive lateral flow test strip mounted in a housing.

One embodiment of an inventive lateral flow test strip with a housing is illustrated in Fig. In FIG. 2 the lateral flow assay device is shown with an upper part which when in place exposes the sample pad to receive the sample and has an opening or window above the capture zone to allow the results of the lateral flow assay to be read As also shown in FIG. 2, this lateral flow test strip has a rectangular shaped sample receiving area which extends beyond the linear array of the analyte capture zones. Extension beyond the capture zones is used to prevent distortion of the signal due to "edge-flow-effects." A preferred embodiment adds "non-interactive" protein (or other macro-molecules) such that there is an edge-to-edge uninterrupted linear array composed of "non-interactive" and "capture-interactive" molecules. This functions to streamline the flow and also to prevent cross-contamination. The phrase "edge-to-edge" means across the whole width of the strip, e.g. from left to right. "Non-interactive" means not involved in target or other analyte capture and "capture-interactive" means involved in the capture of target molecules or other analytes.

The inventive transverse lateral flow test strip may comprise a competition assay, a sandwich assay, an indirect assay, or another type of assay, or a mixture of assay types, known in the art, as well as a simple rapid detection format to detect pre-deposited (e.g. by hybridization, see example 4) analytes/targets on a nitrocellulose (or other lateral flow appropriate membranes). Thus, the analyte capture zones of the lateral flow test strip may comprise the immobilized component of a competition assay, a sandwich assay, or another type of assay, or a mixture of assay types. The transverse lateral flow test strip may contain one or more control zones in order to determine that the device or a particular assay contained on the device worked properly. The elements of a particular assay may be applied to the lateral flow assay test strip of the invention using techniques known in the art. The particular elements are placed between the sample application zone and the capture zone such that the sample flows across the assay elements toward the assay capture zone. Alternatively, part of the assay may be performed in solution prior to applying the mixture to the lateral flow sample pad. For example, a sample may be mixed with a label, such as a UPT or colloidal gold particulate label, prior to application to the lateral flow assay strip.

It should also be noted that conventional assay labels such as, but not limited to, enzyme labels, fluorescent labels, radiolabels, particulate labels, such as colloidal gold and colored latex particles, including those utilized in upconverting phosphor technology, may be utilized on the inventive lateral flow test strips. Additionally, the inventive lateral flow test strips may also use any analyte capturing compositions which provide either or both visual or instrumentally measurable changes when exposed to the target analyte.

Each of the analyte capture zones may bind a different species of analyte, or may bind the same species of analyte. In lateral flow test strips where each of the analyte capture zones binds the same species of analyte, the binding may occur at varying concentrations of analyte.

The inventive lateral flow test strip has linear arrays of the target capture molecules located perpendicular to the sample flow which arrangement avoids non-specific interactions and resulting loss of signal. Instead of conventional striping, target molecules are spotted as dot or disk shaped areas on the strip using conventional automated spotting techniques. The disk or dot volume may vary, from nanoliter to microliter quantities, depending on the desired signal and capture load. Inventive lateral flow test strips are ordinarily wider yet shorter than a conventional sized lateral flow test strip.

The analyte capture zones are disk or dot shaped and in a linear array parallel to the sample receiving area and substantially equidistant from the sample receiving area. In the inventive embodiment shown in FIG. 2, the absorbent pad located at the top of the strip downstream from the sample pad and the capture zones, attracts the sample and solvent flow from the sample receiving area through the analyte capture zones. The test strip may be a single piece strip or constructed of overlapping pads or strips, as is known in the prior art. For example, the sample pad and absorbent pad overlap each 2.5 mm with the nitrocellulose strip to ensure sample flow. After contact with the sample the analyte capture zones are then read visually or by an appropriate scanning instrument by scanning across the lateral flow test strip as shown in FIG. 2. One example of a suitable scanning instrument is the Packard Fluorometer. For assays with up-converting phosphor labels a device such as the Up-Link® reader is preferred.

The invention avoids signal loss from the loss of sample as compared to the conventional lateral flow test strip. Signal loss on conventional lateral flow test strips is believed to occur due to extended and varied sample flow distances and/or non-specific capture by preceding capture zones. On the inventive lateral flow test strips, the multiple target capture zones are positioned substantially equidistant from the sample receiving area, and non-specific capture is avoided by the arrangement of the multiple target capture zones relative to the sample flow path.

The inventive transverse lateral flow test strips can be placed within conventional plastic housing used with conventional lateral flow test strips thereby allowing use of visually read devices or conventional scanners (a prototype device applicable for UPT detection utilizing the UPlink reader is shown in Malamud et al. Adv. Dent. Res., 18:12-16, June 2005). The inventive strips may also have an extended width relative to the conventional lateral flow test strip, for example, of up to about 4 cm. In comparison, a conventional lateral flow test strip is about 0.4 cm in width.

The placement of the inventive lateral flow test strips in a conventional reader results in a scan read direction of the lateral flow test strip perpendicular to the flow of the sample out of the sample receiving area. This is in contrast to the conventional lateral flow test strip which is scanned in the same direction as the flow of the sample out of the sample receiving area.

The wider inventive lateral flow test strips of, for instance, about 4 cm wide, would theoretically allow for the simultaneous analysis of up to 200 target capture zones with a disk or spot size of about 0.1 mm. Further development of the reader technology, for instance, a smaller spot size combined with smaller detection areas, will allow many more additional capture zones. In principle, analyte capture zones can be applied to test strips in volumes ranging from nanoliters to microliters.

This invention also includes a method of analyzing for an analyte comprising the step of applying a sample to a lateral flow test strip. The lateral flow test strip comprises a sample receiving area for receiving a sample for analysis, and two or more analyte capture zones. Specifically, the analyte capture zones are arranged perpendicular to a flow of the sample from the sample receiving area and substantially equidistant to the sample receiving area.

The method of analyzing an analyte may be carried out in a single flow or a multiple flow technique, as is known in the art. See, e.g., Coico, et al., Immunology—A Short Course, 5th Ed. 2003 John Wiley & Sons. In a single flow technique, a fluid sample is applied to the lateral flow assay strip. The lateral flow assay strip itself may contain the assay reagents or the sample may be mixed with one or more reagents before application of the fluid sample to the lateral flow assay strip. A preferred multiple flow technique is known as a "consecutive flow" technique. In a consecutive flow technique, there is a first flow of sample suspected of containing targets of interest allowing enrichment and concentration of specific targets (e.g. HIV antibodies in serum specimen) at the target capture line; an optional intermediate flow with wash buffer to remove all non-specifically bound and non-bound material and to decrease background; followed by a second flow with the reporter. The consecutive flow technique allows for the use of a generic reporter (e.g. a UPT particle or colloidal gold particle covered with protein-A, which interacts with human antibodies). Multiple flows with the short transversal flow strips of the invention works well since the flow rate is faster and flow time as compared to the conventional longer strip is thus much shorter.

Although the foregoing description is directed to the preferred embodiments of the invention, it is noted that other variations and modifications will be apparent to those skilled in the art, and which may be made without departing from the spirit or scope of the invention.

All references cited or mentioned herein are hereby incorporated by reference in their entireties for all purposes.

EXAMPLES

Example 1

DIG-Biotin DNA Dilution Series

A dilution series of DIG-biotin haptenized DNA was mixed with Avidin-D and spotted on the nitrocellulose membrane of conventional strips and inventive strips. The double-stranded DIG-biotin DNA, containing one DIG and one biotin on opposite sites, has a size of 452 bp (base pairs). A dilution series of 12 steps ranking from 15 ng to 7.5 pg (consecutive 2× dilution steps) was mixed with a fixed amount (1 µg) of Avidin-D in PBS (phosphate buffered saline) and incubated at room temperature for 15 minutes. The mixture was spotted on both conventional strips and inventive strips; 0.25 µl was hand-spotted on both types of LF strips [Note that on the conventional strip only the capture zones are located sequentially parallel to the sample pad, and so not all at the same distance from the sample pad]. On the inventive test strip, analyte capture spots were divided from each other by 0.25 µl BSA (bovine serum albumin) (1 µg/µl) spots to prevent cross-contamination of the analyte capture materials and to streamline the particle flow. The strips were allowed to dry for 30 minutes at 37° C. See FIG. 3A for an illustration of the inventive test strip.

Detection was performed with a MαDIGPHOS-conjugate (UPT reporter particles surface coated with monoclonal mouse αDIG antibodies, (in example 4) also referred to as MαDIGUPT) in SRB (standard running buffer, 135 mM NaCl, 1% w/v BSA, 0.5% v/v Tween-20, 10 mM Hepes, pH 7.4). Conventional strips were each analyzed with 100 ng of the phosphor-conjugate in 100 µl SRB, and the inventive strip was analyzed with 1000 ng of phosphor-conjugate in 1000 µl SRB. Since the width of the conventional strips was 4 mm as compared to 4 cm for the inventive strip, the amount of SRB buffer used was proportional to the width of the strip. Flow was continued until both strips were completely dry. The strips were then analyzed in an adapted Packard FluoroCount reader (Niedbala et al., Anal. Biochem., 2001, 293, pp. 22-30) using the scanning software version 5.5.0 for the Packard Fluorometer and UPlink™ reader designed for use with assays using up-converting phosphor labels. See the Corstjens et al. and Malamud et al. articles discussed above.

Figure 4:
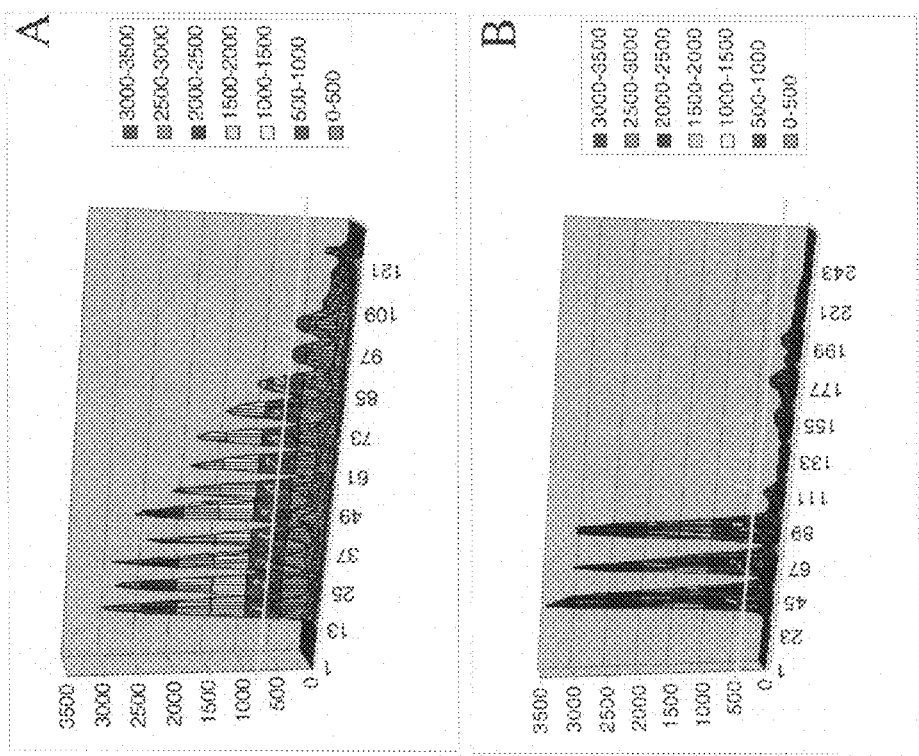
FIGS. 4, 5 and 6 illustrate the results of analytical testing and evaluation of the lateral flow assay devices by UPT analysis of Examples 1, 2 and 3, respectively.

Results:

The results of the experiment are shown in FIG. 4. The dilution series tested on the inventive lateral flow test strip (FIG. 4A) shows signals above the estimated background down to the tenth dilution, or a sensitivity of approximately 30 pg. Under comparable conditions the signal on a conventional lateral flow test strip falls below the estimated cut-off value at the fourth dilution step, or a sensitivity of 4 ng, which is about 100 times less sensitive than the inventive test strip. It should be noted that due to the 50% shorter nitrocellulose membrane, sample flow over the inventive test strip is faster than the conventional test strip.

This example demonstrates that when using multiple capture zones, conventional lateral flow strips are hindered by depletion and/or clogging of the reporter particle flow especially in case the highest signals occur closest to the sample application pad. When using lateral flow assay strips according to the invention, the order (sequence) of the capture zones is of no importance. As a consequence, inventive lateral flow strips avoid the problem of depletion and/or clogging.

Example 2

Target Labeling

Figure 3:
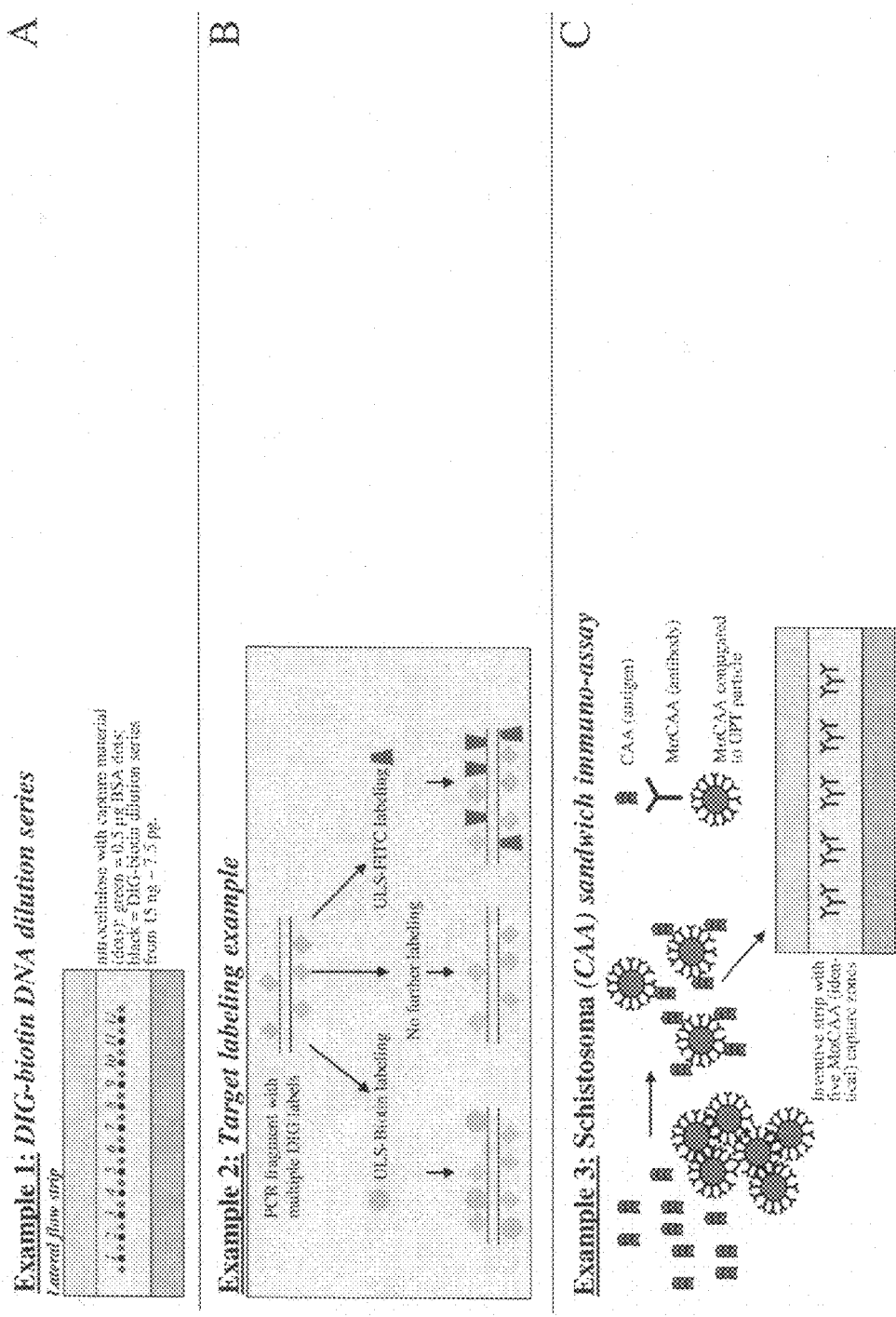
FIG. 3 illustrates the composition and arrangement of components of the lateral flow assay devices of Examples 1, 2 and 3. For Example 2 only the target labeling is shown; the lateral flow strip with capture antibodies on the strips (anti-DDIG, anti-FITC, anti-Biotin and the negative control anti-CAA) are not shown.

A 452 bp HPV fragment was amplified by PCR with primer pair LF65-LF66 (Corstjens et al., Clin Chem., 2001), during amplification DIG-dUTP was incorporated. The resulting multi-DIG labeled DNA fragment (target) was gel purified and divided into three equal parts. One part was an unlabeled control and two parts were labeled; one with a secondary biotin label and another with a secondary FITC label. See FIG. 3B, showing how the target labeling was performed. Biotin and FITC labeling was performed using ULS-biotin and ULS-FITC, respectively, both available from Kreatech Biotechnology, The Netherlands).

Inventive strips containing different capture zones were prepared by spotting on each strip of the present invention, 1 µl of a 1:10 and 1:50 dilution (in 10 mM Tris pH 8, 1% (v/v) MeOH) of mouse monoclonal antibody samples: α-Biotin, α-CAA, α-DIG and α-FITC. The strips were allowed to dry for 30 minutes at 37° C. The α-CAA antibody preparation was selected randomly and used as a negative control to test for non-specific interactions; it is a monoclonal antibody against a circulating antigen from Schistosoma (Decider et al. 1996, Parasitology, 112, pp. 21-35).

Specific capture and detection of differently labeled targets was measured by using DNA samples diluted to 10 ng/µl. From these three DNA samples, five different mixtures were prepared:

mix A containing 10 ng DIG-FITC DNA+20 ng DIG DNA;

mix B containing 10 ng DIG-Biotin DNA+20 ng DIG DNA;

mix C containing 30 ng DIG DNA;

mix D containing 10 ng DIG-Biotin DNA+2.5 ng DIG-FITC DNA+7.5 ng DIG DNA; and mix E containing 10 ng DIG-Biotin DNA+0.25 ng DIG-FITC DNA+9.75 ng DIG DNA.

Note that all mixtures contain the same amount of DNA (30 ng), implying that each mixture would also contain the same amount of DIG hapten. The DNA mixtures (prepared in 250 µl SRB) were each flowed-over an inventive lateral flow test strip. After 5-10 minutes a secondary flow with 500 ng MαDIGPHOS (in 250 µl SRB) was used for detection. The technique described here is an example of a "consecutive flow" technique.

Figure 5:
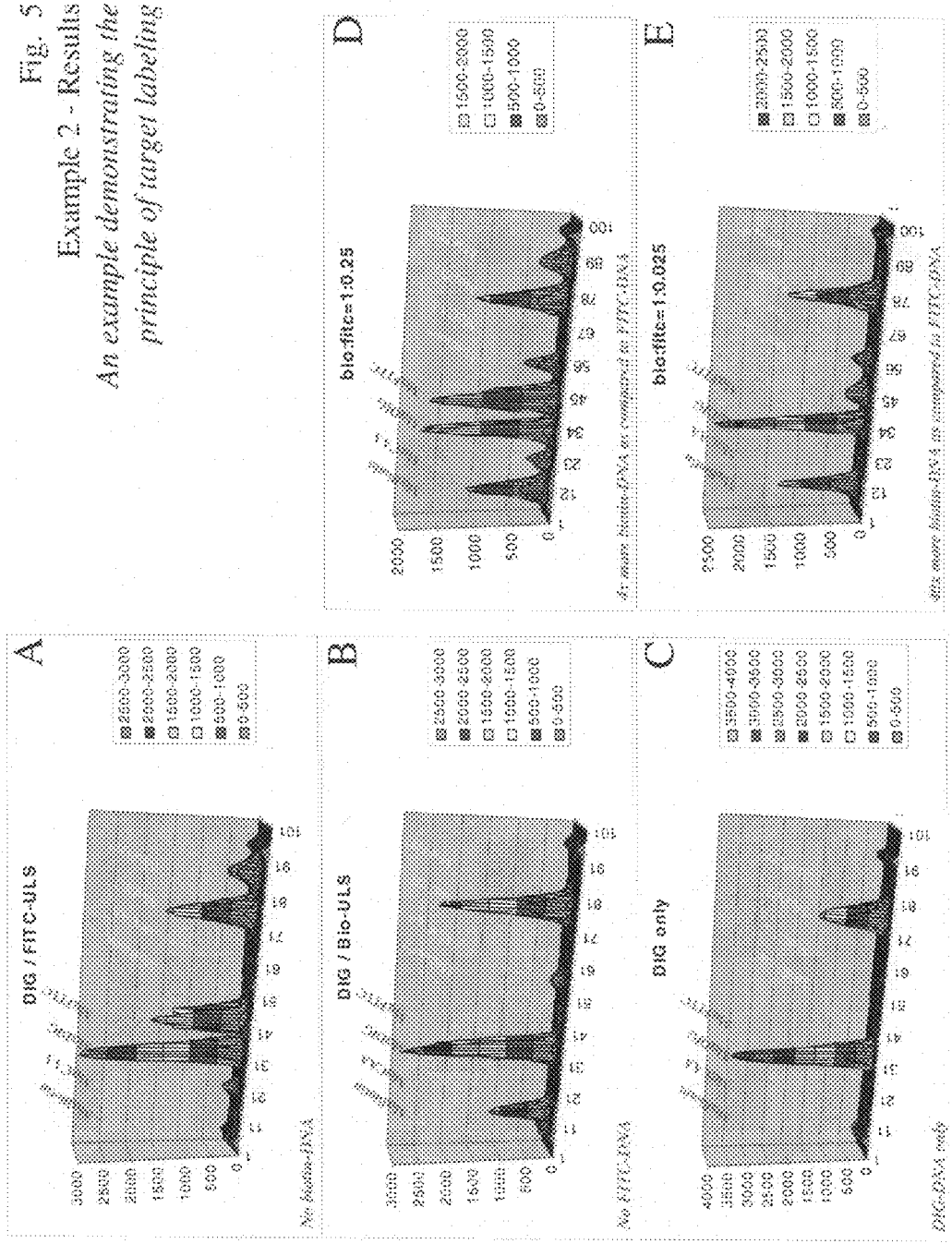

Results:

The results of the experiment are shown in FIG. 5. Note that the graphs are not presented at the same scale, and that the right-hand sides of all test strips contain five times less capture molecules than the left-hand side. The results obtained with mixtures A-C (FIG. 5, panel A-C) indicate that the binding in the different capture-zones on the inventive strips is specific. Only the highest capture load of MαCAA demonstrates some nonspecific binding with MαFITC DNA (FIG. 5, panels A and D). This could be managed by increasing the salt concentration of the running buffer (not shown). Variation of DIG-FITC labeled DNA in the presence of a fixed amount of DIG-Biotin labeled DNA (FIG. 5, panels D and E) does not appear to affect the DIG-Biotin signal. The DIG-FITC signal was semi-quantitative. The experiment demonstrates target labeling techniques using the inventive lateral flow test strips.

Example 3

Schistosoma CAA-Sandwich Immunoassay

Signal reproducibility was tested on an inventive lateral flow test strip prepared with five similar analyte capture spots on one strip. A dilution series to test sensitivity of the CAA-sandwich using the inventive strips was prepared. In a rapid test (FIG. 6, panel A-C) 10 µg, 10 ng and a zero control of CAA antigen were mixed with 500 ng MαCAAPHOS conjugate (in 250 µl SRB). Samples were immediately applied to the inventive lateral flow test strips with five capture zones of MαCAA antibody.

Figure 6:
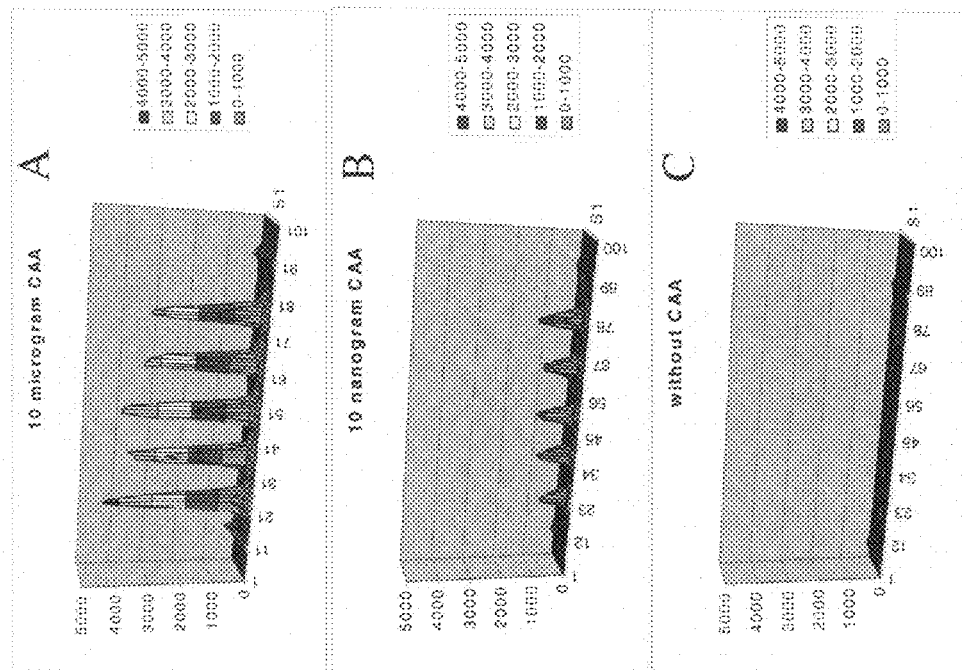

Results:

The results of the experiment are shown in FIG. 6. The results show a distinction between the 10 µg and 10 ng sample. Although the results appear to be quantitative, the signals obtained with 10 µg of CAA apparently suffer from the high-dose-hook effect. All duplicate capture zones (5 per strip) are produced approximately the same signal. The small observed differences were most likely caused by pipetting errors, including, for instance, damaging of the nitrocellulose membrane, and small differences in the distance of the spot from the sample receiving area. The zero control does not indicate any relevant nonspecific interaction.

This example indicates that when the distance from the sample receiving area to the analyte capture spot is kept substantially constant, the actual location of the capture spot along the x-axis of the filter does not affect the intensity of the signal obtained.

Example 4

Binary Typing using One-Dimensional Microarrays

Figure 7:
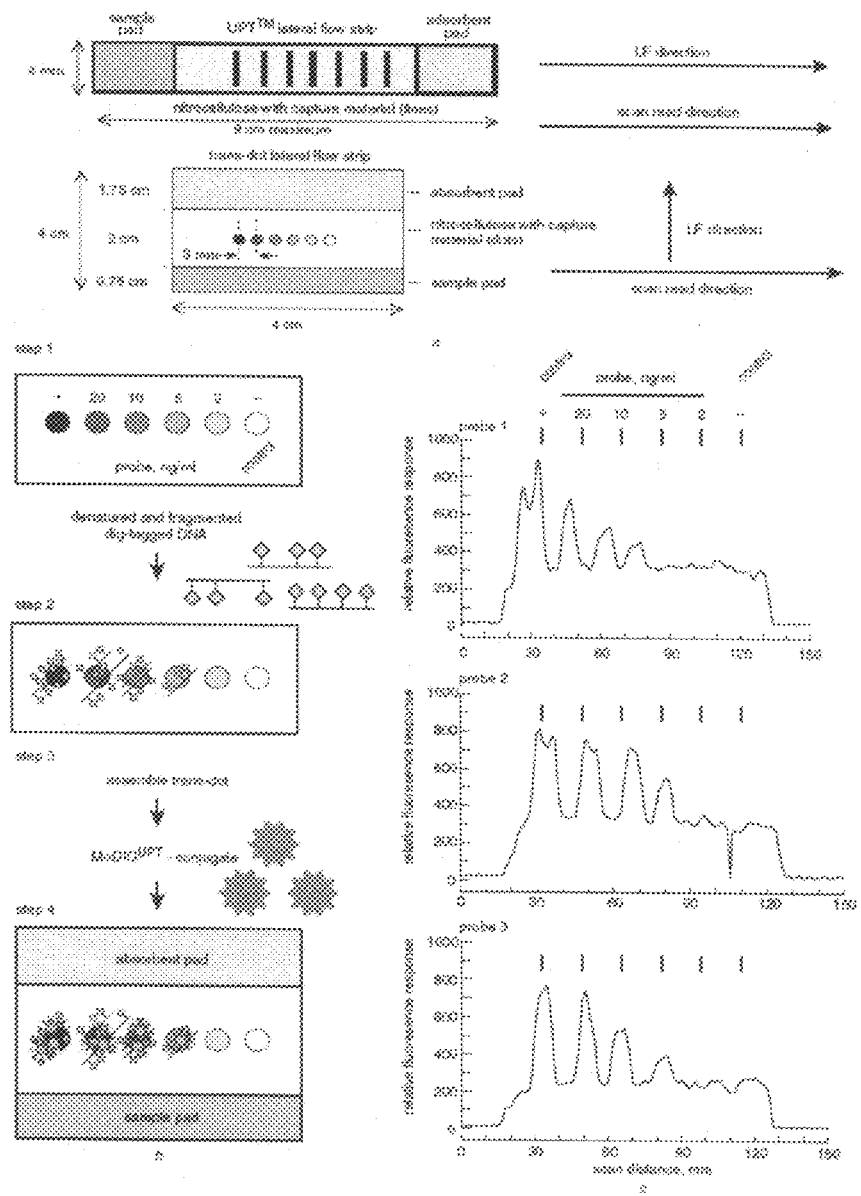
FIG. 7 illustrates a transversal flow format using a one-dimensional array of capture molecules, as described in Example 4.

This example shows the potential of a lateral flow assay system of the invention for rapid detection of multiple hybridized targets. The lateral flow assay system incorporates the transverse flow geometry allowing the use of a one dimensional array of capture zones consisting of a large ($\geqq 20$) selection of probes. This approach employed hapten tagging of the whole pool of nucleic acid material present in a sample followed by a hybridization-based selection of specific targets within that pool. Hybridization events are visualized with a generic UPT-conjugate with antibodies directed against the hapten used to tag the nucleic acid pool. Detection of the presence of a specific nucleic acid target is linked to the UPT-signal obtained at a defined position on the membrane as specific probes were immobilized in a one dimensional array on the membrane (FIG. 7a). Three DNA probes used for the binary genotyping of *Staphylococcus aureus* strains were tested through reversed hybridization with digoxigenin-tagged genomic DNA of a compatible *S. aureus*. After hybridization, membranes were assembled into a trans-dot format and a buffer containing 1 mg of an MαDigUPT conjugate was applied to the sample application pad (FIG. 7b). After a brief chromatography, the sample pad and absorbent pad were removed, the strips air dried and scanned. The resulting profiles (FIG. 7c) demonstrate detectable signals with all three probes at the 5 ng level. The scans shown in FIG. 8c were obtained from membranes hybridized with 200 ng/ml target, digoxigenin-tagged *S. aureus* DNA. Additional experiments indicated that a four-fold reduction of the concentration of DNA to 50 ng was possible. The level of sensitivity obtained with this rapid UPT chromatography detection format is one-order of magnitude better than chromogenic to detection and equal to the detection obtained with chemiluminescent substrates. In addition to binary typing of a particular organism, this format can also be employed to develop a single-test strip for the detection of multiple pathogenic microorganisms and can be readily adapted for the detection of other biological molecules.

The claimed invention is:

1. A lateral flow test strip comprising a sample receiving area for receiving a sample for analysis, and two or more analyte capture zones, wherein each of said two or more analyte capture zones is substantially equidistant to the sample receiving area and arranged in a linear array substantially parallel to the sample receiving area,
    wherein the sample receiving area comprises a sample pad adjacently disposed along the length of said linear array of the analyte capture zones, wherein said sample pad extends beyond the linear array of the analyte capture zones.

2. The lateral flow test strip according to claim 1, wherein each of the analyte capture zones binds a different species of analyte.

3. The lateral flow test strip according to claim 1, wherein each of the analyte capture zones binds the same species of analyte.

4. The lateral flow test strip according to claim 3, wherein each of the analyte capture zones binds the same species of analyte at varying concentrations of analyte.

5. The lateral flow test strip according to claim 1, wherein the sample receiving area is rectangular shaped.

6. The lateral flow test strip according to claim 1, wherein the analyte capture zones contain about 1 nanoliter to about 1 microliter of one or more analyte capturing compositions.

7. The lateral flow test strip according to claim 1, wherein the analyte capturing compositions comprise at least one member selected from the group consisting of binders, antibodies and antigens.

8. The lateral flow test strip according to claim 1, wherein said lateral flow test strip comprises composition for either a competition assay or a sandwich assay.

9. The lateral flow test strip according to claim 1, wherein at least one of said analyte capture zones comprises an immobilized component of a competition assay or a sandwich assay.

10. The lateral flow test strip of claim 1, further comprising an absorbent pad downstream from the sample receiving area and the capture zones.

11. A method of analyzing for an analyte comprising the steps of:
    applying a sample to a lateral flow test strip, wherein the lateral flow test strip comprises a sample receiving area for receiving a sample for analysis and two or more analyte capture zones, wherein the analyte capture zones are substantially equidistant to the sample receiving area and arranged in a linear array substantially parallel to said sample receiving area, wherein the sample receiving area comprises a sample pad adjacently disposed along the length of said linear array of the analyte capture zones, wherein said sample pad extends beyond the linear array of the analyte capture zones;
    performing an analyte binding assay; and
    analyzing said lateral flow test strip for binding of an analyte.

12. The method according to claim 11, wherein each of the analyte capture zones of said lateral flow test strip binds a different species of analyte.

13. The method according to claim 11, wherein each of the analyte capture zones of said lateral flow test strip binds the same species of analyte.

14. The method according to claim 13, wherein each of the analyte capture zones of said lateral flow test strip binds the same species of analyte at varying concentrations of analyte.

15. The method according to claim 11, wherein the sample receiving area of said lateral flow test strip is rectangular shaped.

16. The method according to claim 11, wherein the analyte capture zones of said lateral flow test strip contain about 1 nanoliter to about 1 microliter of one or more analyte capturing compositions.

17. The method according to claim 11, wherein the analyte capturing zones of said lateral flow test strip comprise at least one member selected from the group consisting of binders, antibodies, and antigens.

18. The method according to claim 11, wherein said lateral flow test strip comprises a component of a competition assay, an indirect assay, or a sandwich assay.

19. The method according to claim 11, wherein the analyte capture zones of said lateral flow test strip comprise an immobilized component of a competition assay.

20. The method according to claim 11, further comprising the step of:

washing said lateral flow test strip with buffer to remove any excess or non-specifically bound material.

21. The method according to claim 11, wherein the lateral flow test strip further comprises an absorbent pad downstream from the sample receiving area and the capture zones.

22. The method according to claim 11, further comprising the step of:

applying a label-containing liquid to said lateral flow test strip to detect the presence of an analyte captured in an analyte capture zone.

23. The method according to claim 11, wherein the analyte capture zones of said lateral flow test strip comprise an immobilized component of a sandwich assay.

* * * * *